United States Patent
Ibrahim

(10) Patent No.: US 6,919,200 B2
(45) Date of Patent: *Jul. 19, 2005

(54) PURIFICATION METHOD AND APPARATUS

(75) Inventor: Sofi M. Ibrahim, Frederick, MD (US)

(73) Assignee: The United States of America as represented by the Secretary of the Army, Washington, DC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/444,095

(22) Filed: Nov. 22, 1999

(65) Prior Publication Data

US 2001/0036630 A1 Nov. 1, 2001

Related U.S. Application Data

(60) Provisional application No. 60/109,437, filed on Nov. 23, 1998.

(51) Int. Cl.[7] ............................. C12N 1/08; C12M 1/34; G01N 33/00; G01N 21/00
(52) U.S. Cl. ...................... 435/270; 435/6; 435/287.2; 435/287.9; 436/94; 536/23.1; 422/57; 422/58; 422/99
(58) Field of Search ........................ 435/6, 270, 287.2, 435/287.3, 91.1, 91.2, 270.1; 436/94, 501; 536/23.1; 422/57, 58, 99; 530/587.2

(56) References Cited

U.S. PATENT DOCUMENTS

| | | | |
|---|---|---|---|
| 4,225,575 A | * 9/1980 | Piasio et al. | 424/1 |
| 4,657,869 A | 4/1987 | Richards et al. | 435/287 |
| 4,789,628 A | 12/1988 | Nayak | 435/7 |
| 5,173,260 A | * 12/1992 | Zander et al. | 422/57 |

(Continued)

FOREIGN PATENT DOCUMENTS

| | | | | |
|---|---|---|---|---|
| JP | 0730814 | * 11/1995 | | C12M/1/34 |
| JP | 7-308184 | * 11/1995 | | |
| WO | 94/18564 | * 8/1994 | | |
| WO | WO94 18564 A | 9/1994 | | G01N/33/543 |
| WO | WO95 19447 | 7/1995 | | C12Q/3/00 |

OTHER PUBLICATIONS

Boom et al., Journal of Clinical Microbiology, Mar. 1990, vol. 28, No. 3, pp. 495–503.*

(Continued)

*Primary Examiner*—Bradley L. Sisson
(74) *Attorney, Agent, or Firm*—Elizabeth Arwine

(57) ABSTRACT

A purification apparatus, kit and method for purifying DNA, RNA, proteins, antigens, antibodies and cells. The apparatus has a wand and a reservoir tube. The wand is made of a cap, a sample collection assembly and an elongated shaft connecting the cap to the sample collection assembly. The sample collection assembly has a series of microstructures on its surface, or microparticles enclosed within it for increasing the surface area of the sample collection assembly. The increased surface area permits maximum exposure to and binding of target molecules thereto. The reservoir tube associated with the wand has one end defining an opening and a second end that is closed and preferably cone or cylindrical shaped. The cap of the wand securely and sealingly fastens to the open end of the reservoir tube with the shaft and the sample collection assembly fitting easily inside the reservoir tube. The apparatus, kit and methods can be used for protein and nucleic acids detection by calorimetric, luminescent, fluorescent or electrochemical means through attachments for detecting such signals. The apparatus, kit and methods can also be used in conjunction with an attachment for thermal regulation to perform nucleic acids amplification. The apparatus, kit and methods can further be configured for integrated, high throughput purification and detection of proteins and nucleic acids.

14 Claims, 3 Drawing Sheets

U.S. PATENT DOCUMENTS

| | | | |
|---|---|---|---|
| 5,229,297 A | * | 7/1993 | Schnipelsky et al. .......... 436/94 |
| 5,483,972 A | * | 1/1996 | Nabai et al. ................. 600/562 |
| 5,514,785 A | * | 5/1996 | Van Ness et al. ........... 536/22.1 |
| 5,556,752 A | * | 9/1996 | Lockhart et al. ................ 435/6 |
| 5,591,841 A | * | 1/1997 | Ji et al. ...................... 536/25.4 |
| 5,637,687 A | * | 6/1997 | Wiggins .................... 536/25.4 |
| 5,665,582 A | | 9/1997 | Kausch ........................ 435/181 |
| 5,962,218 A | | 10/1999 | Leland ........................... 435/6 |
| 6,020,186 A | * | 2/2000 | Henco et al. ............. 435/287.2 |
| 6,228,578 B1 | * | 5/2001 | Impraim et al. ................ 435/6 |
| 2003/0204077 A1 | * | 10/2003 | Simms ....................... 536/25.4 |

OTHER PUBLICATIONS

Boom et al., "Rapid and Simple Method for Purification of Nucleic Acids," Journal of Clinical Microbiology, Mar. 1990, vol. 28, No. 3, pp. 495–503.*

Boom et al., "Rapid and Simple Method for Purification of Nucleic Acids," Journal of Clinical Microbiology, Mar. 1990, vol. 28 No. 3, pp. 495–503.*

* cited by examiner

PURIFICATION METHOD AND APPARATUS

This application claims the benefit of provisional application Ser. No. 60/109,437 filed an Nov. 23, 1998.

BACKGROUND OF THE INVENTION

1. Field of the Invention

This invention relates to a method, an apparatus, and kit for performing purification of nucleic acids, proteins and cells. More specifically, the invention relates to an apparatus and methods for purification and concentration of nucleic acids, proteins (e.g., antigens and antibodies) and cells without the need of centrifugation, precipitation or lengthy incubations. The apparatus and methods can be adapted to non-specific or specific capture of nucleic acids, proteins or cells in a biological or environmental samples and can be adapted for detection of the captured moiety by enzymatic calorimetric, fluorescent, luminescent or electrochemical formats with or without nucleic acids amplification.

2. Description of Related Art

Nucleic acids preparation and purification is essential to virtually all molecular biology. Most methods in use for purifying nucleic acids rely on labor-intensive organic extractions and/or centrifugation. In recent years, a new class of analytical and purification techniques have been developed which rely on the inherent biological affinities between proteins, between enzymes and their substrates, and between proteins and nucleic acids.

Affinity techniques are attractive because the desired molecules are rapidly and specifically immobilized away from the other contaminating molecules in an impure mixture, offering rapid and extensive purification or enrichment levels. Contaminating molecules are simply washed away, while target molecules remain firmly affinity-bound. Target molecules may be detached from their counterpart molecules simply by altering the environment to disfavor the affinity between the two.

In one technique, a solid phase support is used to attach target molecules from a sample, such as DNA, RNA, proteins or cells. The solid phase support can also be coated with specific oligonucleotides, peptide or cell receptors to capture a specific DNA, RNA or protein molecules as well as whole cells or microorganisms. Such solid phase supports consist generally of material with selective adsorption, ion exchange and catalytic properties. When such solid phase supports are formed by deep reactive ion etching (DRIE), they can provide exceptionally large surface area, high levels of activity and selectivity in a wide range of reactions, for example to nonspecifically capture electrically charged molecules, or specifically capture molecules through affinity binding. Examples of solid phase supports include silica-based material, synthetic polymers and a host of other naturally-occurring or chemically modified elements.

Chemical modification may be achieved by incorporating metal atoms, e.g., Li, Be, Mg, Co, Fe, Mn, Zn, B, Ga, Fe, Ge, Ti, Au, Pt or As into a solid support framework consisting of, for example, $Si^{4+}$ and $Al^{3+}$. In a typical application of a solid support system to directly capture nucleic acids molecules, for example, is to mix a biological sample with a guanidine-based lysis/binding solution in the reservoir, the sample capture assembly is inserted into the reservoir, sealed, the entire apparatus is briefly vortexed, agitated or sonicated, briefly incubated at the appropriate temperature, e.g., 37° C. (the shaft may also be thermally regulated through an attachment to a miniaturized thermal regulator) to allow the released nucleic acids to adsorb or bind to the capture assembly. Mechanical disruption (by vortexing, sonication or shaking) or enzymatic disruption (e.g., by lysozymes, proteinase K, collagenase) may be required for some biological samples to enhance the release of nucleic acids.

After the nucleic acids are released and captured onto the capture assembly by virtue of electrical charge or affinity binding, the capture assembly is removed, placed into another reservoir containing wash buffer with appropriate salt concentration and ionic strength (e.g., 1.0 M NaCl, 50 mM MOPS, 15% ethanol, pH 7.0 for DNA), sealed and briefly vortexed or agitated. Several washes can be performed in the same reservoir by replenishing the wash buffer if multiple washing is necessary to remove undesirable or inhibitory material from the captures nucleic acids. The removal of undesirable or inhibitory material can enhance subsequent nucleic acids amplification steps.

After washing, the reservoir is replaced with a fresh reservoir containing elution buffer with appropriate salt concentration and ionic strength (e.g., 1.25 M NaCl, 50 mM Tris/HCl, 15% ethanol, pH 8.5 for DNA), and the capture assembly is inserted into the reservoir, incubated at the appropriate temperature, e.g., 65° C. for several minutes (or the capture assembly is subjected to the appropriate elution temperature through the thermal regulator attachment). Alternatively, it is possible to perform thermal cycling through the thermal regulator attachment while the DNA is initially bound to the capture assembly with the appropriate nucleic acids amplification buffer and reagents placed in the reservoir. The Lysis/binding, washing and elution buffer conditions may be adapted according to the sample type and the type of the nucleic acids (DNA or RNA).

However, the solid phase supports currently available do not provide vast surface area to maximize binding of molecules. In addition, they are expensive to make, and do not lend themselves to in-home or field use because of either their size or configuration. Furthermore, they do not allow the flexibility of purifying different types of molecules, e.g., nucleic acids, proteins or whole cells in a single format with the ability to capture such molecules specifically or nonspecifically, and detect such molecules (specially nucleic acids) with or without nucleic acids amplification using calorimetric, fluorescent, luminescent or electrochemical formats. The present invention, in toto, allows much greater flexibility and efficiency and is adaptable to future modification by, for example, incorporating thermal cycling amplification (e.g. PCR), isothermal amplification and fluorogenic, calorimetric, luminescence or electrochemical detection in the same device. The present invention also allows incorporation of specific capture molecules, e.g. dendritic (branched) oligonucleotides or peptides to further increase the capture surface area and allow the specific capture of nucleic acids, cells or proteins. In addition, the invention can be adapted to an arrayable platform to allow high throughput sample processing and detection in the same device.

What is lacking in the art is a simple, inexpensive apparatus, flexible kit and method for DNA, RNA, protein, antigen, antibody or cell purification that can be used in the field, home or laboratory with the flexibility described above. In particular, what is needed is an apparatus and method that does not require centrifugation, precipitation, lengthy incubations, or extensive equipment and that provides a massive surface area for maximum exposure to and binding of target molecules. With an increasing desire to perform rapid testing for a variety of infectious disease agents or biological markers in the home, field or by medical and health care workers, there is a need to provide a simple, flexible and easy to use apparatus, kit and methods for purification and detection.

It is therefore an object of the invention to provide a simple method, apparatus and kit for conducting DNA, RNA, protein or cell purification.

It is a further object of the invention to provide an apparatus that is convenient to use in the home or in the field that provides high precision and good economy.

It is still a further object of the invention to provide an apparatus that provides efficient purification of nucleic acids, proteins, or cells with out the need for centrifugation, precipitation or lengthy incubations.

It is a further object of this invention to provide an apparatus that is adaptable for direct detection of nucleic acids and proteins by calorimetric, fluorogenic, luminescence or electronic means or detection of nucleic acids molecules after nucleic acids amplification in such an apparatus.

It is a further object of this invention to provide an apparatus and concept that is a adaptable for rapid, flexible high through put screening of biological samples or biological products for infectious disease agents and biomarkers.

These and other objects are achieved with the method, apparatus and kit of the present invention.

SUMMARY OF THE INVENTION

The present invention is summarized as an apparatus for purifying DNA, RNA, proteins (antigens and antibodies) or cells and is adaptable for detection of such moieties by a variety of detection formats with a wide range of applications in the medical diagnostics, counter bioterrorism and the health care arena. The apparatus has a wand and a reservoir tube (e.g., a microfuge tube). The wand is made of a cap, a sample collection assembly and an elongated shaft connecting the cap to the sample collection assembly. The sample collection assembly has a series of microstructures on its surface or microparticles enclosed within it for increasing the surface area of the sample collection assembly. The increased surface area permits maximum exposure to and binding of target molecules thereto.

The reservoir tube associated with the wand has one end defining an opening and a second end that is closed. The cap of the wand securely and sealingly fastens to the open end of the reservoir tube with the shaft and the sample collection assembly fitting easily inside the reservoir tube.

In use, for nucleic acids applications, a sample is placed inside a first reservoir tube with a lysis or denaturing solution. Then the wand is inserted into the first reservoir tube. The cap of the wand secures and seals closed the first reservoir tube. The first reservoir tube is agitated by shaking or vortexing to mix the sample with the denaturing solution. During this step, the target molecules bind to the sample collection assembly's massive surface area. The wand, which now has target molecules attached to the sample collection assembly is then removed from the first reservoir tube and inserted into a second reservoir tube which contains a wash buffer.

The second reservoir tube is then securely and sealingly closed with the cap of the wand like before. The second reservoir tube is also agitated to mix the sample with the wash buffer. The wand is then removed from the second reservoir tube and inserted into a third reservoir tube. The third reservoir tube contains an elution buffer.

The third reservoir tube; is incubated and after a short while, the DNA or RNA is purified. It can then be recovered and analysed.

A similar process is used for the capture of antigens, antibodies or cells, however different reagents or buffers are used.

Agitation or sealing is not required during the incubation steps as long as the capture assembly is in contact with the sample. However, agitation may enhance binding and sealing would help contain the sample in the reservoir and prevent accidental loss of the sample or contaminating the sample from an outside source.

DETAILED DESCRIPTION

The present invention is directed to a purification apparatus for purifying Nucleic acids, proteins, microorganisms or cells.

Figure 1A:
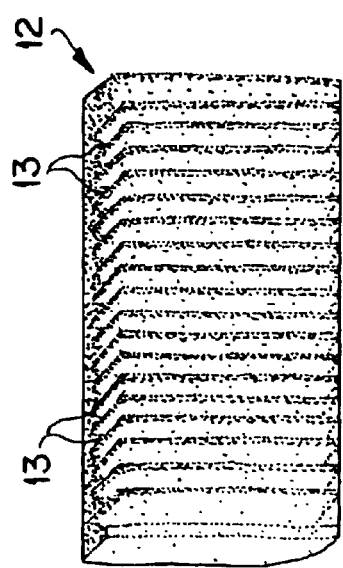
FIG. 1a is an enlargement of the flange 12 shown in FIG. 1.
Figure 1:
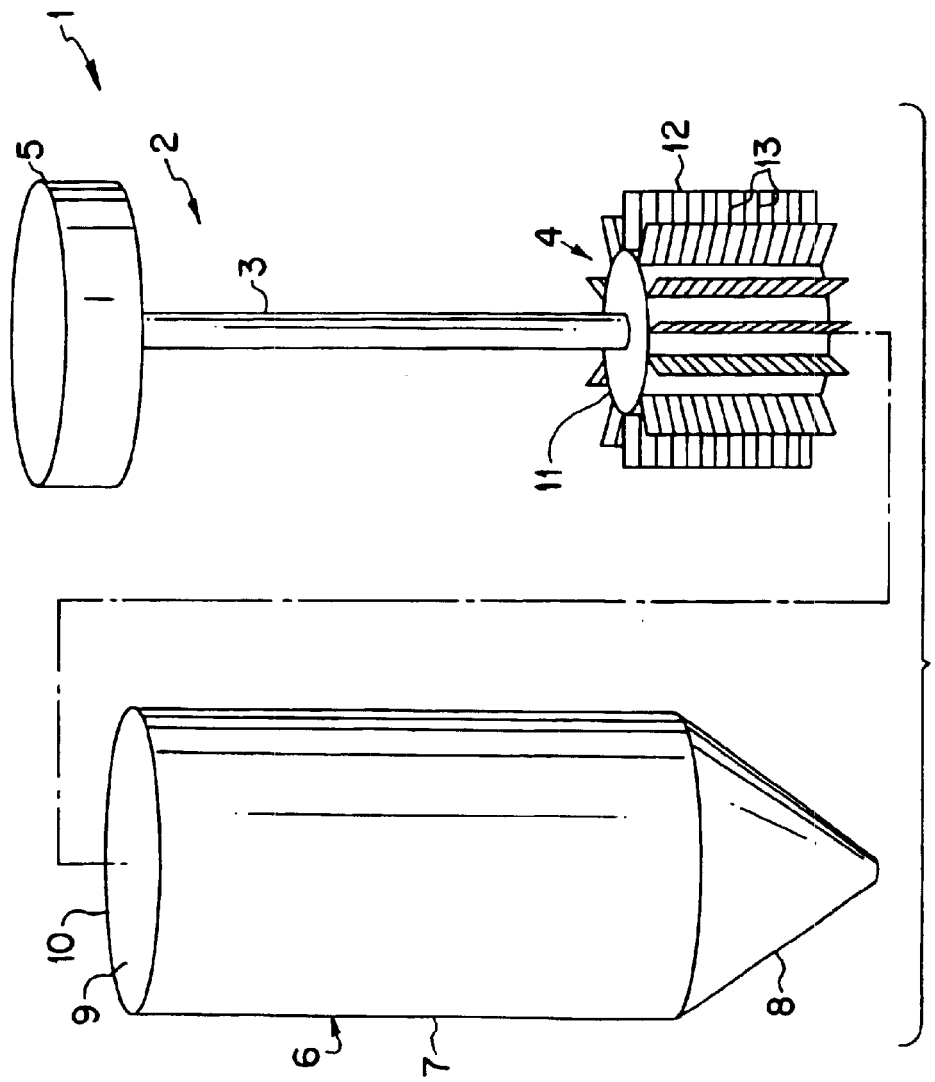
FIG. 1 is a perspective view of a Purification Apparatus according to a first embodiment of the invention.

Referring to FIG. 1, the purification apparatus 1 has a wand 2 and a reservoir tube 6. The wand 1 is made of a cap 5, a sample collection assembly 4 and an elongated shaft 3 connecting the cap 5 to the sample collection assembly 4. The sample collection assembly 4 has a series of microstructures 13 in the form of grooves (created by deep reactive ion etching or tooling), parallel lanes or cross-etchings on its surface, or microparticles 13a (See FIG. 2) enclosed within it for increasing the surface area of the sample collection assembly 4. The increased surface area permits maximum exposure to and binding of target molecules thereto, allowing concentration of target molecules or cells.

Figure 4:
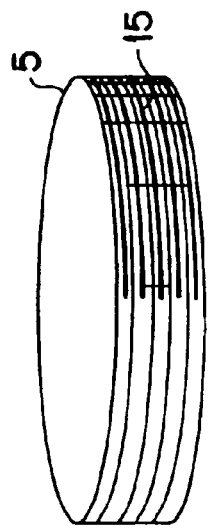
FIG. 4 is perspective view a screw on cap.
Figure 5:
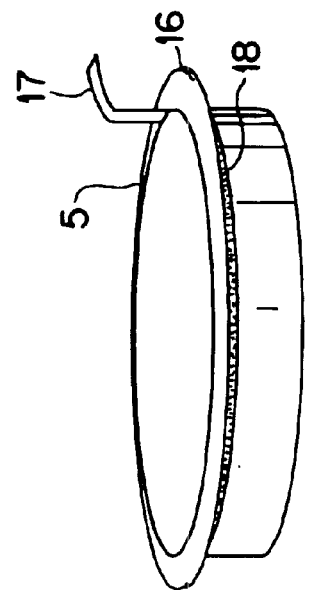
FIG. 5 is a perspective view of a snap-on cap.

The cap 5 of the wand 1 is easily held between the forefinger and the thumb of a user. The cap configuration reduces the risk of contamination because the user's fingers do not come into contact with the sample capture assembly. The cap fits snugly into the open end 9 at the lip 10 of the reservoir tube 6. Referring to FIGS. 4 and 5, the cap 5 can be formed with screw-on ridges 15 for screwing the cap 5 into the reservoir tube 6. In this embodiment, the reservoir tube has complimentary grooves (not shown) therein for receiving a screw-on cap in a sealing engagement. Alternatively, the cap 5 can have a stopper lip 16 and can fit into the reservoir tube 6 and be held in place in a sealed fashion by the force of friction or by a ridge 18 with a complimentary groove (not shown) inside the reservoir tube for receiving the ridge 18. A tab 17 assists the user in removing the wand from the reservoir tube 6 as shown in FIG. 5.

The cap 5 is connected to one end of a shaft 3. The other end of the shaft is connected to a sample capture assembly 4. The shaft 3 is either solid or hollow and can be formed of metal or an inert synthetic material such as plastic. The sample capture assembly 4 is designed to increase surface area to a maximum to allow maximum exposure to and binding of target molecules thereto. Therefore, the sample capture assembly 4 has microstructures associated therewith, either on its surface or within it in the form of microparticles enclosed inside a mesh enclosure in a form of a "molecular sieve". If microparticles are used, further enhancements, e.g., the use of zeolitic particles, can be made to allow molecular size selection.

Figure 3:
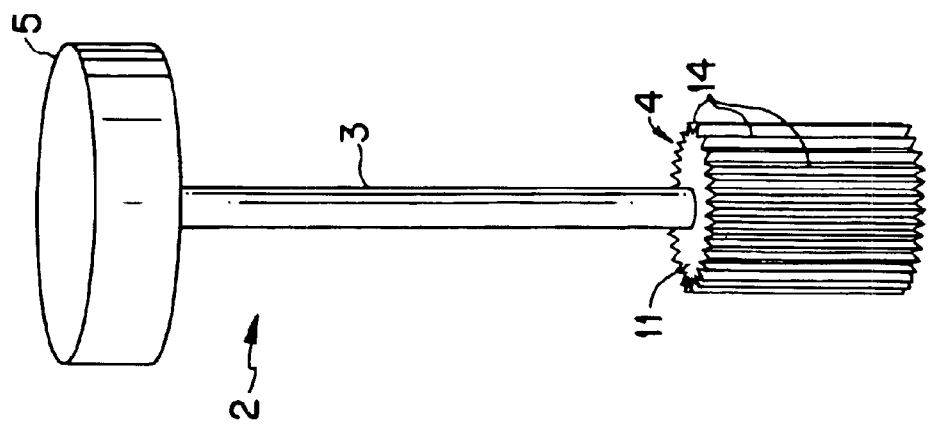
FIG. 3 is a perspective view of a Purification Apparatus according to a third embodiment of the invention.

The sample capture assembly 4 is generally a main body 11 having microstructures on its surface in the form of cross-etched lanes, dimples, domes, pillars and/or pores. Such microstructures can be formed by tooling or etching. Preferably, cross-etched lanes in the configuration presented herein are used as microstructures and are etched to a depth of 0.001–2 mm and preferably 2 mm. The main body 11 can preferably have one or more flanges 12 protruding radially outward therefrom, wherein the microstructures 13 are on an outer surface of the flanges 12. FIG. 1a shows an enlargement of a single flange 12. Alternatively, the main body can have striations 14, wherein a cross-section of the main body 11 would reveal a jagged outer edge as shown in FIG. 3. The striations increase the surface area and preferably also have microstructures on their outer surface. The main body 11 can also be porous.

Figure 2:
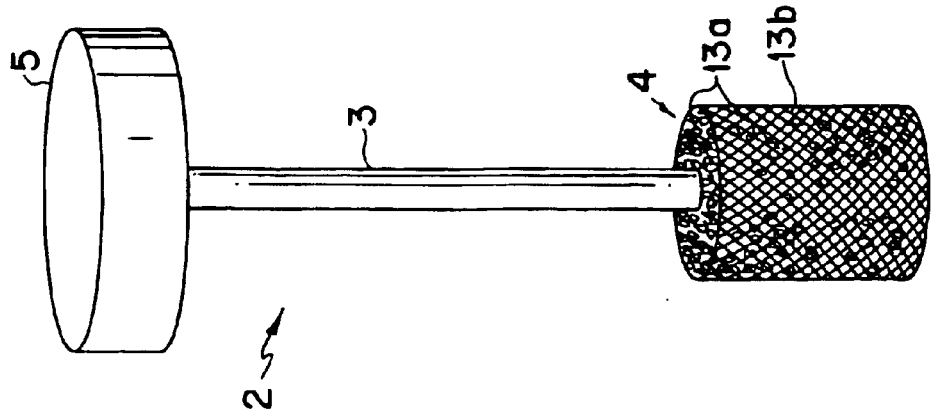
FIG. 2 is a perspective view of a Purification Apparatus according to a second embodiment of the invention.

Still further, FIG. 2 shows a wand 2 having a sample capture assembly 4 that has microstructures 13a associated therewith within it in the form of microparticles enclosed inside a mesh enclosure 13b. The microparticles are made from silica-based material, polystyrene or other synthetic polymers and may be coated with a target specific surface such as specific oligonucleotides, peptides or cell receptors to capture a target DNA, RNA, protein or cell type. They are preferably about 1 to 500 μm in diameter.

The sample collection assembly 4 may be coated with oligonucleotide probes or specific proteins to capture specific target molecules. The sample collection assembly may also be made of or coated with a material that binds non-specifically with nucleic acids or proteins. A suitable material for binding non-specifically to nucleic acids include silica-based material such as silicon oxide and aluminum oxide and synthetic polymers. However, a host of other naturally occurring or chemically modified elements that are known to bind non-specifically to nucleic acids or proteins may be used. The sample collection assembly can also be coated with gold, platinum or other material to enhance electrical or electrochemical conductivity. The sample collection assembly can also be coated with singular or dendritic oligonucleotide probes, peptide probes or cell receptors to capture specific target molecules. The use of dendritic probes in conjunction with the sample collection assembly described herein can further significantly increase the capture surface area and significantly enhance analytical and clinical sensitivity.

The capture of nucleic acids, proteins or cells either non-specifically or by affinity binding onto solid phase supports as well as colorimetric, luminescent, fluorescent and electrochemical detection are well known in the art as described in the following and other references, of which these are herein incorporated by reference: Ausubel F., Brent R., Kingston R. E., Moore D. D., Seidman J. G., Smith J. A., Struhl K., (1987). Current Protocols in Molecular Biology. Greene Publishing Associates and Wiley-Intersciences. John Wiley & Sons, New York, Chichester, Brisbane, Toronto, Singapore.; Sambrook J., Fritsch E F, Maniatis J. (1989). Molecular cloning: A laboratory manual. $2^{nd}$ edition, Cold Spring Harbor laboratory Press, Cold Spring Harbor, N.Y.; Homes E., Korsnes L. (1990). Magnetic DNA hybridization properties of oligonucleotide probes attached to superparamagnetic beads and their use in the isolation of poly(A) mRNA from eukaryotic cells. Genet. Anal. Tech. Appl. 7:145–150.; Jakobsen K. S., Haugen M., Saeboe-Larsen S., Hollung K., Espelund M., Hornes E. (1994). Direct mRNA isolation using magnetic Oligo(dT) beads: A protocol for all types oc cell cultures, animal and plant tissues. In: Advances in Biomagnetic Separation, (Ed. Uhlen M., Hornes E., Olsvik O) Eaton Publishing pp.61–71.; Rodriguez I. R., Chader G. J. (1992). A novel method for the isolation of tissue specific genes. Nucleic Acids Res. 18:4833–4842.; Schussler P., Gohr L. G., Sommer G., Kunz W., Grevelding C. G. (1995). Combined isolation of nucleic acids and proteins from small amounts of tissue. Trends Genet. 11:378–379.; Beattie K. L., Fowler R. F. (1991). Solid-phase gene assembly. Nature 352:548–552.; Rudi K., Kroken M., Dahlberg O. J., Deggerdal A., Jakobsen K. S., Larsen F. (1997). Rapid, universal method to isolate PCR-ready DNA using magnetic beads. BioTechniques 22:506–511.; Collin-Osdoby P., Oursler M. J., Webber D., Osdoby P. (1991). Osteoclast-specific monoclonal antibodies coupled to magnetic beads provide a rapid and efficient method of purifying avian osteoclasts. J. Bone Mine. Res. 6:1353–1365.; Cudjoe K. S., Krona R., Olsen E. (1994). IMS: A new selective enrichment technique for the detection of salmonella in foods. Int. J. Food Microbiol. 23:159–165.; Elgar G. S., Brenner S. (1992). A novel method for isolation of large insert DNA from recombinant lambda DNA. Nucleic Acids Res. 20:4667.; Gabrielsen O. S., Huet J. (1993). Magnetic DNA affinity purification of yeast transcription factor. Meth. Enzymol. 218:508–525.; Hames B. D., Higgins S. J. (1985). Nucleic acid hybridization: A practical approach. IRL Press, Oxford, England.; Hawkins R. E., Russell S. J., Winter G. (1992). Selection of phage antibodies by binding affinity. Mimicking affinity maturation. J. Mol. Biol. 226:889–896.; Boom, R., Sol, C. J., Salimans, M. M., Jansen, C. L., Wertheim-van Dillen, P. M., and van der Noordaa, J. (1990). Rapid and simple method for purification of nucleic acids. J. Clin. Microbiol., 28(3):495–503.; Lundeberg J., Larsen F. (1995). Solid-phase technology:magnetic beads to improve nucleic acid detection and analysis. Biotechnology Annual Review 1:373–401.; Millar D. S., Withey S. J., Tizard M. L. V., Ford J. G., Hermon-Taylor J. (1995). Solid-phase hybridization capture of low abundance target DNA sequences: application to the polymerase chain reaction detection of Mycobacterium paratuberculosis and Mycobacterium avium susp. Silvaticum. Anal. Biochem. 226:325–330.; Vlieger A. M., Medenblik A. M. J. C., Van Gijlswijk R. P. M., Tanke H. J., Van der Ploeg M., Gratama J. W., Raap A. K. (1992). Quantitation of polymerase chain reaction products by hybridization-based assays with fluorescent, calorimetric or chemiluminescent detection. Anal. Biochem. 205:1–7.

The reservoir tube 6 serves as a reservoir for collecting samples, washing the captured nucleic acids, proteins, antibodies or antigens, and eluting the captured nucleic acid or proteins or other molecules. The reservoir tube 6 described herein has an elongated body 7 with one end having a lip 10 defining an opening 9 and a second end 8 that is closed and preferably cone shaped. The second end 8 can also be rounded or cylindrical. The cap 5 of the wand 2 securely and sealingly fastens to the open end 9 of the reservoir tube 6 with the shaft 3 and the sample collection assembly 4 fitting easily inside the reservoir tube 6. The reservoir tube typically holds 0.5–15 ml of sample and preferably is a 1.5 ml reservoir tube. The reservoir tube can be larger or smaller without detracting from the spirit of the invention. The reservoir can also be designed in the form of a microtiter plate or microtiter plate modules to allow arrayable, modular configuration.

The reservoir tube is made of a size to enclose the shaft and sample capture assembly of the wand and sealingly engage the wand's cap. The reservoir and wand can be manufactured together and be packaged as a kit with multiple reservoir (tubes of different sizes and shapes or microtiter plates) in each kit. The wand can be manufactured in a size to fit reservoirs of different sizes and shapes that are commercially sold on the market and commonly used in biomedical research.

Figure 6:
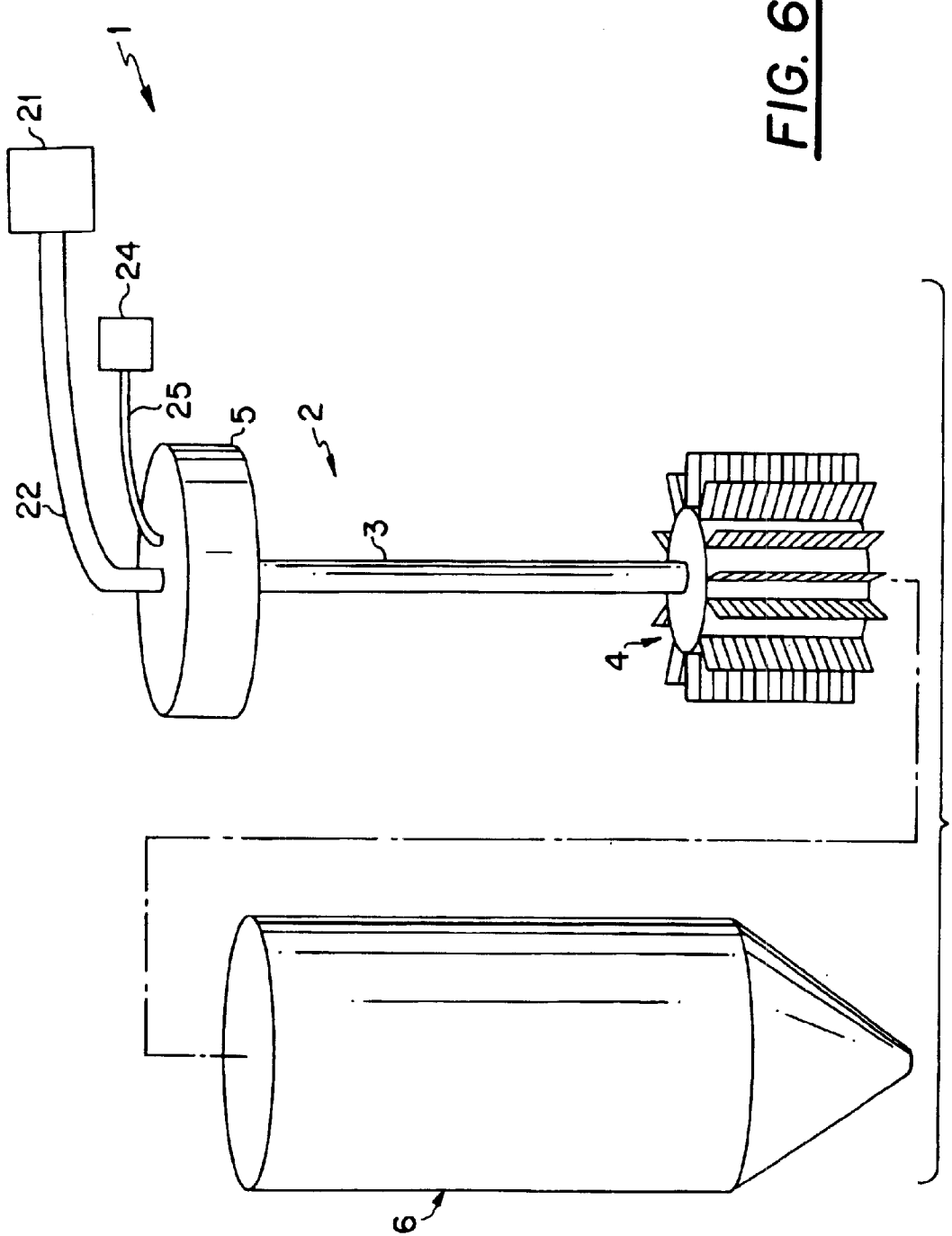
FIG. 6 is a perspective view of a Purification Apparatus according to the invention showing a heating unit and a sensing unit.

In use, a sample is placed inside a first reservoir tube with a lysis or denaturing solution. By the term DNA or RNA sample, it is meant a sample, usually cells, that contain DNA or RNA within the cells. Then the wand is inserted into the first reservoir tube. The cap of the wand secures and seals closed the first reservoir tube. The first reservoir tube is agitated by shaking or vortexing to mix the sample with the denaturing solution. The first tube is preferably incubated at 37° C. for a period of 5–15 minutes. The shaft of the wand can be thermally regulated through an attachment or wire connection 22 to a heating unit 21 as shown in FIG. 6. During this step, the target molecules bind to the massive surface area of the sample collection assembly.

The wand, which now has target molecules bound to the sample collection assembly is then removed from the first reservoir tube and inserted into a second reservoir tube which contains a wash buffer. The second reservoir tube is then securely and sealingly closed with the cap of the wand as before. The second reservoir tube is also agitated to mix the sample with the wash buffer. One or several washes can be performed in the same reservoir if multiple washing is necessary to remove inhibitory material from the captured nucleic acids. The wand is then removed from the second reservoir tube and inserted into a third reservoir tube. The third reservoir tube contains an elution buffer. The third reservoir tube is incubated at about 65° C. for about 5–15 minutes with or without agitation or vortexing (agitation or vortexing may enhance elution). If the shaft is attached to a heating unit that regulates temperature in the sample capture assembly, elution can be achieved by adjusting the incubation temperature. After a short while, the DNA or RNA is purified. It can then be recovered and analyzed. It is also possible to perform thermal cycling while the captured DNA is bound to the capture assembly, and the elution buffer is replaced with the appropriate nucleic acid amplification buffer and reagents.

The sample can be detected by one of several methods. DNA or amplified DNA can be detected by known calorimetric, luminescent, fluorescent or electrochemical methods.

In another embodiment, the wand may further have a sensing unit 24 associated with it via a sensing contact or wire connection 25 as shown in FIG. 6 for sensing electrical or electrochemical signals emitted from the sample on the sample collection assembly, following a hybridization and/or an enzymatic reaction. Such a sensing unit would detect changes in electrical properties of bound nucleic acids or protein molecules either directly or indirectly. Direct detection can be achieved by measuring changes in current subsequent to a hybridization reaction. Indirect detection can be achieved by including in the hybridization reaction an enzyme and a substrate to drive a reduction/oxidation reaction resulting in electrical current change which can be measured by an electric current sensing device, for example. Alternatively, other indirect reaction may involve enzymatic reaction to produce calorimetric, fluorogenic or luminescence signal which can be detected with miniature optical devices such as a flurometer or spectrometer designed to fit the closed end of the reservoir. In this embodiment, the tube would fit into such a detection device wherein the detection would take place.

The purification apparatus of the invention can be used for efficient purification of nucleic acids, proteins and cells without the need of centrifugation, precipitation or lengthy incubations. It can also be configured to allow nucleic acid amplification and detection by integrating the purification apparatus into an instrument that allows temperature cycling and detection apparati capable of fluorescent, calorimetric, luminescent or electrochemical sensing.

EXAMPLES

Example 1
Nucleic Acid Purification

In a typical nucleic acids purification, mix 10–100 $\mu$l of sample with 100 $\mu$l of lysis/denaturing buffer in a 1.5 ml reservoir tube. Insert the shaft and sample capture assembly of the wand into the reservoir tube and close the reservoir tube with the cap. Vortex the reservoir tube for about 1 minute. Incubate the reservoir tube at 37° C. for about 5 minutes. Remove the wand, and insert the wand into a fresh reservoir tube containing 1000 $\mu$l of wash buffer. Vortex the reservoir tube for about 1 minute. Remove the wand and insert it into a fresh reservoir tube containing 100 $\mu$l of elution buffer. Heat the reservoir tube to abut 65° C. for about 5 minutes. The DNA or RNA is now purified and ready for further analysis or processing.

Example 2
Nucleic Acids Detection

Detection of nucleic acids can be performed in a variety of formats. For example, after the captured nucleic acids are eluted into the reservoir, a biotin- and a digoxigenin-labeled probes can be hybridized, a streptavidin-coated capture assembly is immersed into the reservoir to capture they hybrid complex, then an antibody against digoxigenin is added to bind to the digoxigenin-labeled probe, then an enzyme labeled secondary antibody is added to bind to the primary antibody, then a chemiluminescent or calorimetric substrate is added to drive a colorimetric or luminescent reactions which can then be detected with a calorimeter, photoluminometer or by an electric current measuring device. A number of washing steps must be performed between the addition of reagents in the same or different reservoirs to remove unbound molecules. These hybridization and detection methods are known in the art.

It is also possible to configure the detection assays so that the captured nucleic on the sample collection assembly is hybridized in situ to a tagged protein-DNA probe and proceed with the detection according to methods that known in the art.

It is also possible to configure the detection assays so that fluorescently-labeled probes are used for hybridization and detection according to known methods.

Example 3
Antigen Capture and Detection

Mix 10–100 $\mu$l of sample with 100 $\mu$l of lysis/denaturing buffer in a 1.5 ml reservoir tube. Insert the shaft and sample capture assembly (after coating with appropriate antibody) of the wand into the reservoir tube and close the reservoir tube with the cap. Vortex the reservoir tube for about 1 minute. Incubate the reservoir tube at 37° C. for about 5–15 minutes. Remove the wand, and insert the wand into a fresh reservoir tube containing 1000 $\mu$l of blocking buffer. Vortex the reservoir tube for about 1 minute. Incubate at 37° C. for about 5–15 minutes. Remove the wand and insert it into a fresh reservoir tube containing 100 $\mu$l of conjugate solution.

Remove the wand, and insert the wand into a fresh reservoir tube containing 1000 µl of wash buffer. Shake or agitate for 1 min. Discard wash buffer and repeat the washing step. Remove the wand and insert it into a fresh reservoir tube containing 100 µl of detection reagent. Analyze the color and determine the antigen according to a color chart. Alternatively, the color can be read by using a spectrophotometer. The detection step can also be modified to allow electrochemical, luminescent or fluorescent detection using an appropriate signal detection attachment.

Example 4
Antibody Capture and Detection

Mix 10–100 µl of sample with 100 µl of lysis/denaturing buffer in a 1.5 ml reservoir tube. Insert the shaft and sample capture assembly (after coating with appropriate antigen) of the wand into the reservoir tube and close the reservoir tube with the cap. Vortex the reservoir tube for about 1 minute. Incubate the reservoir tube at 37° C. for about 5–15 minutes. Remove the wand, and insert the wand into a fresh reservoir tube containing 1000 µl of blocking buffer. Vortex the reservoir tube for about 1 minute. Incubate at 37° C. for about 5 minutes. Remove the wand and insert it into a fresh reservoir tube containing 100 µl of conjugate solution. Remove the wand, and insert the wand into a fresh reservoir tube containing 1000 µl of wash buffer. Discard the wash buffer and repeat the washing step. Remove the wand and insert it into a fresh reservoir tube containing 100 µl of detection reagent. Analyze the color and determine the antibody. Alternatively, the color can be read by using a spectrophotometer. The detection step can also be modified to allow electrochemical, luminescent or fluorescent detection using an appropriate signal detection attachment.

The present purification apparatus also has applications in detection of blood chemistry, detection of chemokines and other disease markers and identification of microbial agents.

Having thus described in detail preferred embodiments of the present invention, it is to be understood that the invention defined by the appended claims is not to be limited by particular details set forth in the above description as many apparent variations thereof are possible without departing from the spirit or scope of the present invention.

What is claimed is:

1. A method of DNA or RNA purification comprising:
    placing a DNA or RNA containing sample in a first reservoir tube with a solution to effect release of DNA or RNA from cells in said sample;
    inserting a wand into said first reservoir tube, wherein said wand comprises a cap, a sample collection assembly and an elongated shaft connecting said cap to said sample collection assembly, said sample collection assembly having microstructures for increasing the surface area of the sample collection assembly;
    securely and sealingly closing said first reservoir tube with said cap of said wand with said shaft and said sample collection assembly inside said first reservoir tube;
    agitating said first reservoir tube to mix said sample with said solution under conditions for releasing said DNA or RNA front cells in said sample and non-specifically binding said DNA or RNA to said microstructures of said sample collection assembly, thereby non-specifically binding said DNA or said RNA to said microstructures of said sample collection assembly;
    removing said wand from said first reservoir tube and inserting said wand into a second reservoir tube, said second reservoir tube containing a wash buffer;
    securely and sealingly closing said second reservoir tube with said cap of said wand with said shaft and said sample collection assembly inside said second reservoir tube;
    agitating said second reservoir tube to mix said sample with said wash buffer under conditions to retain only said DNA or said RNA on said microstructures;
    removing said wand front said second reservoir tube and inserting said wand into a third reservoir tube, said third reservoir tube containing an elution buffer, wherein said elution buffer causes release of said nucleic acids from said microstructures;
    incubating said third reservoir tube; and
    recovering purified DNA or RNA from said third reservoir tube.

2. The method of claim 1, wherein said sample capture assembly comprises a main body having one or more flanges with microstructures for binding target molecules.

3. The method of claim 2, wherein said microstructures are selected from the group consisting of cross-etched lanes, dimples, pillars and pores.

4. The method of claim 1, wherein said microstructures are selected from the group consisting of cross-etched lanes, dimples, pillars and pores.

5. The method of claim 1, wherein said sample collection assembly comprises a mesh outer surface wherein said microstructures are microparticles enclosed within said mesh outer surface.

6. The method of claim 1, wherein said microstructures of said sample collection assembly are coated with a material that binds non-specifically with nucleic acids.

7. The method of claim 6, wherein said material is silicon oxide or aluminum oxide.

8. The method of claim 1, wherein said microstructures comprise deep reactive ion etchings or toolings that provide an increased surface area on said sample collection assembly.

9. A method of purifying specific DNA or RNA comprising:
    placing a purified DNA or RNA sample in a first reservoir tube under conditions to denature double stranded DNA or render RNA suitable for binding;
    inserting a wand into said first reservoir tube, wherein said wand comprises a cap, a sample collection assembly and an elongated shaft connecting said cap to said sample collection assembly, said sample collection assembly having microstructures for increasing the surface area of the sample collection assembly, and said microstructures of said sample collection assembly are coated with a coating comprising sequence specific oligonucleotide probe, peptide nucleic acid probe through a linker arm, or biotin-streptavidin bond to capture specific target DNA or RNA;
    securely and sealingly closing said first reservoir tube with said cap of said wand with said shaft and said sample collection assembly inside said first reservoir tube, and incubating said DNA or said RNA of the sample in the sample collection assembly under conditions whereby stable, specific hybridization structures are formed, thereby binding said specific DNA or said specific RNA to said coating on said microstructures of said sample collection assembly;
    removing said wand from said first reservoir tube and inserting said wand into a second reservoir tube, said second reservoir tube containing a wash buffer;
    securely and sealingly closing said second reservoir tube with said cap of said wand with said shaft and said sample collection assembly inside said second reservoir tube;

agitating said second reservoir tube to mix said sample with said wash buffer under conditions to retain only said DNA or said RNA on said microstructures;

removing said wand from said second reservoir tube and inserting said wand into a third reservoir tubes said third reservoir tube containing an elution buffer to effect release of said DNA or said RNA;

incubating said third reservoir tube;

removing said sample collection assembly from said third reservoir tube;

recovering said specific DNA or RNA from said third reservoir tube.

10. The method of claim 9, wherein said conditions for denaturing DNA or rendering RNA suitable for binding comprise: heating said reservoir tube for a sufficient time to denature said double stranded DNA or render said RNA suitable for binding.

11. The method of claim 9, wherein said microstructures comprise deep reactive ion etchings or toolings that provide an increased surface area on said sample collection assembly.

12. The method of claim 9, wherein said DNA coating is single stranded DNA and double stranded hybridization structures are formed.

13. The method of claim 9, wherein said DNA coating is double stranded DNA and triplex hybridization structures are formed.

14. A method of purifying specific DNA or RNA comprising:

placing a purified DNA or RNA sample in a first reservoir tube under conditions to denature double stranded DNA or render RNA suitable for binding;

inserting a wand into said first reservoir tube, wherein said wand comprises a cap, a sample collection assembly and an elongated shaft connecting said cap to said sample collection assembly, said sample collection assembly having microstructures for increasing the surface area of the sample collection assembly, and said microstructures of said sample collection assembly are coated with a coating comprising sequence specific oligonucleotide probe, peptide nucleic acid probe through a linker arm, or biotin-streptavidin bond to capture specific target DNA or RNA;

securely and sealingly closing said first reservoir tube with said cap of said wand with said shaft and said sample collection assembly inside said first reservoir tube, and incubating said DNA or said RNA of the sample in the sample collection assembly under conditions whereby stable, specific hybridization structures are formed, thereby binding said specific DNA or said specific RNA to said coating on said microstructures of said sample collection assembly;

removing said wand from said first reservoir tube and inserting said wand into a second reservoir tube, said second reservoir tube containing a wash buffer;

securely and sealingly closing said second reservoir tube with said cap of said wand with said shaft and said sample collection assembly inside said second reservoir tube;

agitating said second reservoir tube to mix said sample with said wash buffer under conditions to retain only said DNA or said RNA on said microstructures;

removing said wand from said second reservoir tube and inserting said wand into a third reservoir tube;

heating said third reservoir tube under conditions to effect release of said DNA or said RNA from said microstructures;

removing said sample collection assembly from, said third reservoir tube; and recovering said specific DNA or RNA from said third reservoir tube.

* * * * *